(12) United States Patent
Lee

(10) Patent No.: US 10,456,311 B2
(45) Date of Patent: Oct. 29, 2019

(54) EXCRETA DISPOSAL APPARATUS PROVIDED WITH ROTARY NOZZLE

(71) Applicant: CURACO, INC., Seongnam-si, Gyeonggi-do (KR)

(72) Inventor: Hoonsang Lee, Seoul (KR)

(73) Assignee: Curaco, Inc., Seongnam-Si, Gyeonggi-Do (KR)

( * ) Notice: Subject to any disclaimer, the term of this patent is extended or adjusted under 35 U.S.C. 154(b) by 145 days.

(21) Appl. No.: 15/548,168

(22) PCT Filed: Feb. 3, 2015

(86) PCT No.: PCT/KR2015/001116
§ 371 (c)(1),
(2) Date: Aug. 2, 2017

(87) PCT Pub. No.: WO2016/125927
PCT Pub. Date: Aug. 11, 2016

(65) Prior Publication Data
US 2018/0021197 A1    Jan. 25, 2018

(51) Int. Cl.
*A61G 9/02* (2006.01)
*A61G 9/00* (2006.01)
(Continued)

(52) U.S. Cl.
CPC .............. *A61G 9/02* (2013.01); *A47K 10/48* (2013.01); *A61F 5/451* (2013.01); *A61G 9/00* (2013.01); *A61G 9/003* (2013.01); *B05B 3/02* (2013.01)

(58) Field of Classification Search
CPC . A61G 9/00; A61G 9/02; A61G 9/003; A47K 10/48; A61F 5/451; B05B 3/02
(Continued)

(56) References Cited

U.S. PATENT DOCUMENTS

| 6,554,817 B1 * | 4/2003 | Oki .................... A61F 5/451 |
| | | 4/455 |
| 2003/0093856 A1 * | 5/2003 | Tanaka ................ A61G 9/003 |
| | | 4/450 |

(Continued)

FOREIGN PATENT DOCUMENTS

| JP | 2003153931 A | 5/2003 |
| KR | 100797578 B1 | 1/2008 |

(Continued)

OTHER PUBLICATIONS

Int'l Search Report dated Sep. 21, 2015 in Int'l Application No. PCT/KR2015/001116.

*Primary Examiner* — Huyen D Le
(74) *Attorney, Agent, or Firm* — Panitch Schwarze Belisario & Nadel LLP

(57) ABSTRACT

An excreta disposal apparatus includes a body having a seating unit correspondingly shaped to the curved shape of the genital area and buttocks of a human body and also has a disposal space open toward the genital area and buttocks of the human body to receive excreta discharged from the human body. A main body unit, for mounting between the legs of the human body, is connected to the seating unit and has an accommodation space therein. A discharge channel, provided in the accommodation space, communicates with the disposal space to discharge the excreta in the disposal space to the outside. A spray unit is exposed to the disposal space to spray washing water, wherein the spray unit comprises a washing unit having a rotary nozzle rotatable about a central axis and having, in the circumference thereof, spray holes for spraying the washing water.

10 Claims, 9 Drawing Sheets

(51) Int. Cl.
     *A47K 10/48*     (2006.01)
     *B05B 3/02*      (2006.01)
     *A61F 5/451*    (2006.01)

(58) Field of Classification Search
     USPC .............................................. 4/443
     See application file for complete search history.

(56) References Cited

U.S. PATENT DOCUMENTS

2009/0193573 A1* 8/2009 Nakamura ............... A61G 7/02
                                                                                         4/320
2017/0172831 A1* 6/2017 Sang ........................ A61G 9/02

FOREIGN PATENT DOCUMENTS

| KR | 20120097946 A | 9/2012 |
| KR | 20140142812 A | 12/2014 |
| WO | 2008038485 A1 | 4/2008 |

* cited by examiner

EXCRETA DISPOSAL APPARATUS PROVIDED WITH ROTARY NOZZLE

CROSS-REFERENCE TO RELATED APPLICATION

This application is a Section 371 of International Application No. PCT/KR2015/001116, filed Feb. 3, 2015, which was published in the Korean language on Aug. 11, 2016, under International Publication No. WO 2016/125927 A1, the disclosure of which is incorporated herein by reference.

TECHNICAL FIELD

The present invention relates to an excreta disposal apparatus for automatically disposing an excreta discharged from a human body, and more particularly, to an excreta disposal apparatus provided with a rotary nozzle that can wash a large area of a disposing space.

BACKGROUND ART

In general, since the patients or the elderly, who have mobility difficulties or who are unable to move their lower body by their own will, do not have the ability to handle their own excreta, there is an inconvenience that a guardian or a caregiver should always reside at hand.

Therefore, in order to solve such an inconvenience, an excreta disposal apparatus for collecting excreta by directly contacting the body has been researched and developed. Such an excreta disposal apparatus is designed to receive and suck a user's excreta and discharge the excreta to the outside so that the excreta can be automatically treated even if the guardian or the caregiver does not reside around the user.

However, since the disposal apparatus is designed without considering the body of the user and is concentrated only on the function of the excreta disposal, the conventional excreta disposal apparatus developed to date has a problem that the usability is very low. Generally, since a part around the buttocks or the genital area where excreta is excreted is sharply curved and the excreta disposal apparatus is difficult to adhered, there are many cases where the excreta leaks out between the human body and the excreta disposal apparatus.

In addition, the users, such as the patients or the elderly, who use the excreta disposal apparatus often live in a bed and frequently cannot change their posture on their own. When such a state persists for a long time, a bedsore occurs, so that it is necessary to periodically change the posture. However, since the posture cannot be changed in the state where the excreta disposal apparatus is worn, there is an inconvenience to remove the excreta disposal apparatus.

In addition, when the user discharges the excreta to the excreta disposal apparatus, much effort is required to wash it. In order to solve this problem, a nozzle for spraying washing water may be provided in a space in which the excreta is received. However, in this case, since the washing can be performed only in a restricted area, the effect is insignificant, and the number of nozzles is inevitably increased.

Therefore, a method for solving such problems is required.

DISCLOSURE

Technical Problem

The present invention has been made in view of the above problems, and provides an excreta disposal apparatus capable of preventing leakage of excreta while a user wears the excreta disposal apparatus, and improving the feelings of wearing.

The present invention further provides an excreta disposal apparatus which can be free from the limitation of the behavior even when the user wears the excreta disposal apparatus.

The present invention further provides an excreta disposal apparatus which can smoothly perform washing of the excreta disposal space and maintain cleanliness.

The problems of the present invention are not limited to the above-mentioned problems, and other problems not mentioned can be clearly understood by those skilled in the art from the following description.

Technical Solution

In an aspect, there is provided an excreta disposal apparatus provided with a rotary nozzle, the apparatus including: a body including a seating unit, which has a shape corresponding to a curved shape of genital area and buttocks of a human body and also has a disposal space open toward the genital area and buttocks of the human body so as to take excreta discharged from the human body, and a main body unit, which is connected to the seating unit so as to be mounted between legs of the human body and has an accommodation space therein; a discharge channel, which is provided in the accommodation space and communicates with the disposal space so as to discharge the excreta in the disposal space to the outside; and a spray unit exposed to the disposal space so as to spray washing water, wherein the spray unit comprises a washing unit comprising the rotary nozzle which is provided so as to rotate about a central axis and sprays the washing water.

A spray hole for spraying the washing water is formed in a circumference of the rotary nozzle.

The disposal space includes a urine disposal unit corresponding to the genital area of the human body and an excrement disposal unit corresponding to the buttocks of the human body, and the rotary nozzle is exposed to the excrement disposal unit.

The rotary nozzle is provided at a position corresponding to a user's anus in a state where the user's body is seated on the seating unit.

In the rotary nozzle, a center of rotation angle of the area exposed to the excrement disposal unit is provided at a position corresponding to the user's anus.

The washing unit includes: a motor which generates a rotational driving force; and a gear unit which is rotated by the motor and transmits a rotational force to the rotary nozzle.

The washing unit includes a shielding member which receives a part of a rear side of the rotary nozzle and shields the inside of the accommodation space from the disposal space.

The apparatus further includes a controller which controls the washing unit.

The apparatus further includes a flow channel switching unit which is provided in the accommodation space and supplies the washing water introduced from an external to the spray unit.

The apparatus further includes an air blowing unit which is provided in the accommodation space and blows a dry air to the disposal space.

The apparatus further includes a detection sensor which is provided in the disposal space and senses the excreta.

Advantageous Effects

In order to solve the above-described problems, the present invention provides an excreta disposal apparatus provided with a rotary nozzle having the following effects.

First, since the seating unit is formed to correspond to the curved shape of the genital area and buttocks of a user and can be adhered to the user's body, there is an advantage that the leakage of the excreta can be prevented in a state where the user wears the excreta disposal apparatus.

Secondly, since the main body unit also has a size corresponding to the width between the legs of the user, there is an advantage that the posture of the user can be maintained naturally.

Third, there is an advantage that the user's feelings of wearing is greatly improved.

Fourth, there is an advantage that the user is not restricted in the behavior even when the user wears the excreta disposal apparatus, and the posture can be freely changed.

Fifth, since the rotary nozzle rotates at a wide angle and can spray the washing water, a large area of the disposal space can be washed. Therefore, it has an excellent cleanliness maintenance effect.

Sixth, since the rotary nozzle can be formed to be self-washable. Therefore, it can reduce the number of washing operations of the entire apparatus.

The effects of the present invention are not limited to the effects mentioned above, and other effects not mentioned can be clearly understood by those skilled in the art from the description of the claims.

MODE FOR INVENTION

Figure 1:
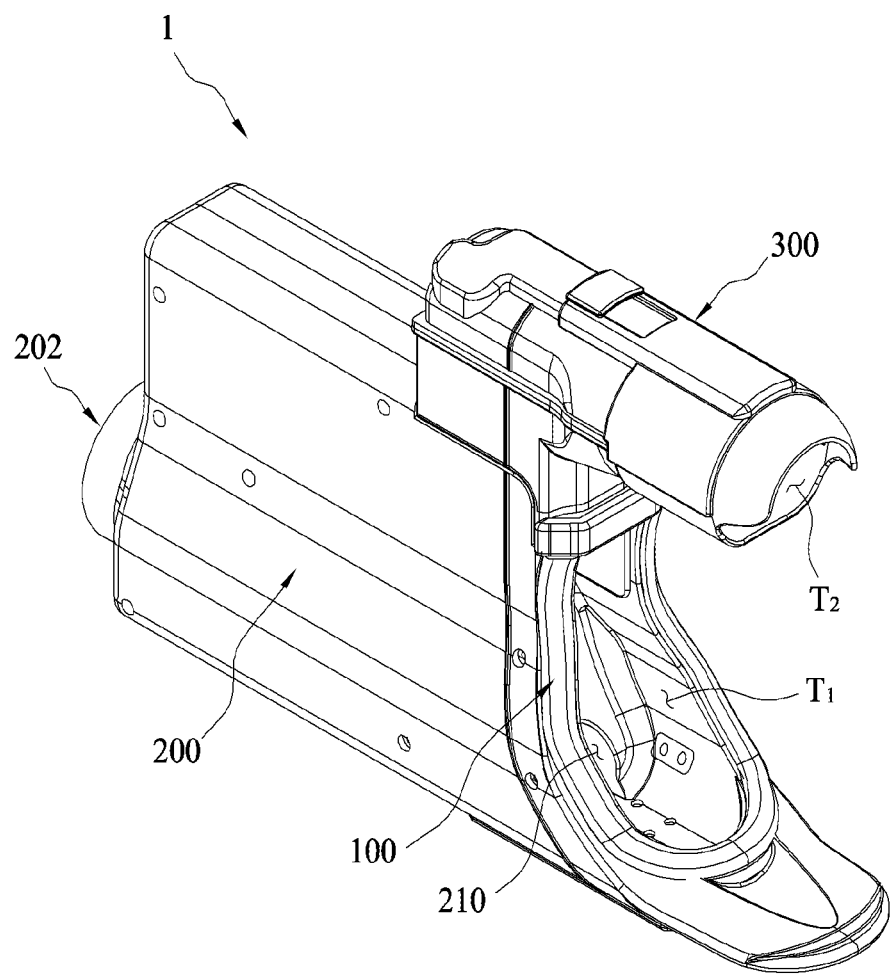
FIG. 1 is a perspective view showing an entire structure of an excreta disposal apparatus according to an embodiment of the present invention.

Hereinafter, preferred embodiments of the present invention will be described with reference to the accompanying drawings. In describing the present embodiment, the same designations and the same reference numerals are used for the same components, and further description thereof will be omitted.

FIG. 1 is a perspective view showing an entire structure of an excreta disposal apparatus 1 according to an embodiment of the present invention.

As shown in FIG. 1, the excreta disposal apparatus 1 according to an embodiment of the present invention includes a body including a seating portion 100 and a main body unit 200, and a discharge channel 210.

The seating portion 100 has a curved shape corresponding to a curvature of the genital area and buttocks of a human body, and has disposal spaces T1 and T2 which are opened in the direction of the genital area and buttocks and receive the excreta discharged from the human body.

Here, the genital area of the human body refers to an area around the sexual organ of the male and female, and the buttocks are connected to the above-mentioned genital area and refers to an area around the anus. That is, the seating portion 100 is formed to be seated in the groin of the human body, and has a curved shape corresponding to the curvature.

The disposal spaces T1 and T2 are formed to have a certain volume so as to receive excreta including urine and excrement. The disposal spaces T1 and T2 of the present embodiment include a urine disposal unit T2 corresponding to the genital area of the human body and an excrement disposal unit T1 corresponding to the buttocks of the human body.

That is, in the case of the present embodiment, the disposal spaces T1 and T2 are partitioned by a male module 300 so as to separately dispose of urine and excrement. However, it is obvious that, when using the excreta disposal apparatus 1 by a woman, unlike the present embodiment, a female module may be used instead of the male module 300. In the case of the female module, the urine disposal unit and the excrement disposal unit may be connected without being partitioned. In addition, unlike the present embodiment, the male module 300 and the female module may be integrally formed without being separated.

The main body unit 200 is connected to the seating portion 100 so as to be mounted between the legs of the human body when a user wears the excreta disposal apparatus 1. That is, the user can stretch his/her legs to both sides of the main body unit 200 in a state in which the seating portion 100 is in close contact with the genital area and buttocks, so that the user can wear the excreta disposal apparatus 1 stably.

In addition, although not shown in the drawing, an accommodation space is provided inside the main body unit 200, and various elements may be provided in the accommodation space. This will be described later.

Meanwhile, for convenience of explanation, the open direction side of the disposal spaces T1 and T2 is defined as a front side, and the opposite direction is defined as a rear side. Further, the direction in which the urine disposal unit T2 is provided is defined as an upper side and the opposite direction is defined as a lower side.

The discharge channel 210 is provided in the accommodation space and communicates with the disposal spaces T1 and T2 to discharge the excreta of the disposal spaces T1 and T2 to the outside. Particularly, in the present embodiment, a through hole 202 is formed in the rear side of the main body unit 200 so that an external connection pipe can be inserted into the accommodation space.

The connection pipe may include an excreta flow pipe connected to suck excreta by using a separate suction device, a washing water feeding pipe for supplying washing water, and the like. That is, the discharge channel 210 is connected to the excreta flow pipe so that the excreta can be discharged to the outside.

Figure 2:
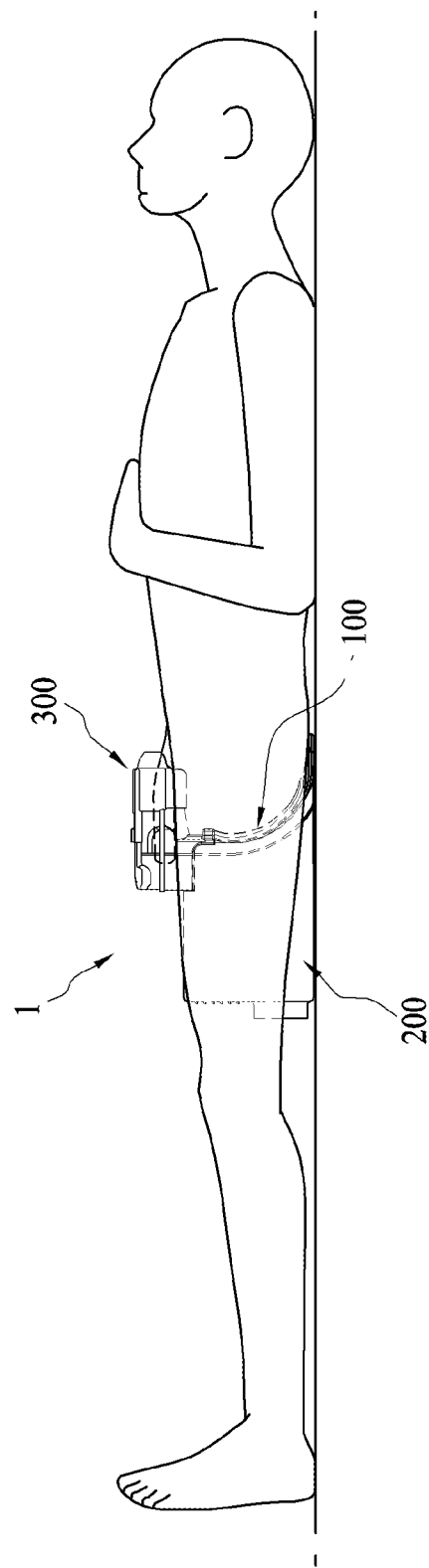
FIG. 2 is a side view of an excreta disposal apparatus worn on a human body according to an embodiment of the present invention.

FIG. 2 is a side view of an excreta disposal apparatus 1 worn on a human body according to an embodiment of the present invention.

As shown in FIG. 2, the user adheres the seating portion 100 to the genital area and buttocks while lying on a bed or the like, and stretches legs on both sides of the main body unit 200 to stably wear the excreta disposal apparatus. As described above, since the excreta disposal apparatus 1 according to an embodiment of the present invention is formed to correspond to the shape of the human body, there is no need for the user to change the posture forcibly according to the excreta disposal apparatus 1, and a natural posture can be maintained.

In addition, even if the user changes his/her posture from side to side or the like, it can be moved along the user's body without being detached, and does not interfere with user's movement in a state of being positioned between the user's legs even when the user moves.

Figure 3:
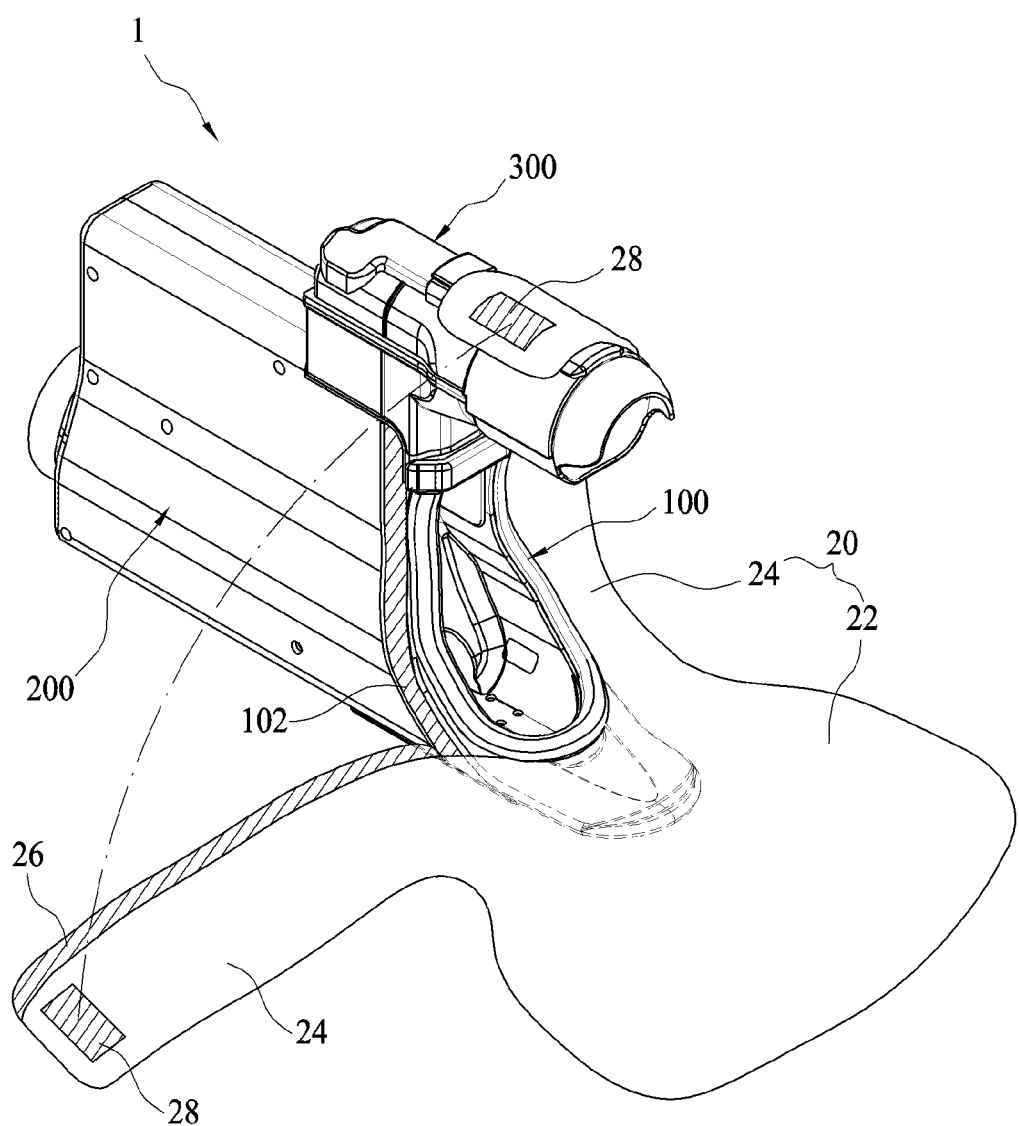
FIG. 3 is a perspective view showing a state where a pad is attached to a seating unit of an excreta disposal apparatus according to an embodiment of the present invention.

FIG. 3 is a perspective view showing a state where a pad 20 is attached to the seating portion 100 of the excreta disposal apparatus 1 according to an embodiment of the present invention.

As shown in FIG. 3, the excreta disposal apparatus 1 according to an embodiment of the present invention may include a pad 20 detachably installed to surround the seating portion 100. The pad 20 may be made of fabric or the like to improve the wearer's feeling of wearing, and may stably fix the excreta disposal apparatus 1 to the user's body.

In the case of the present embodiment, the pad 20 includes a pack portion 22 and a wing portion 24. The pack portion 22 is attached to the lower side of the seating portion 100 so as to surround the circumference of the user's buttocks. The wing portion 24 is attached so as to surround the circumference of the seating portion 100. Meanwhile, in order to attach the pad 20 to the seating portion 100, the seating portion 100 and the pad 20 may be provided with a velcro. That is, a seating unit velcro 102 and a pad velcro 26 are formed to correspond to each other, so that the pad 20 can be easily attached. In addition, in the present embodiment, each wing portion 24 is provided with a fixation velcro 28 so that respective wing portions 24 can be fixed to each other.

Figure 4:
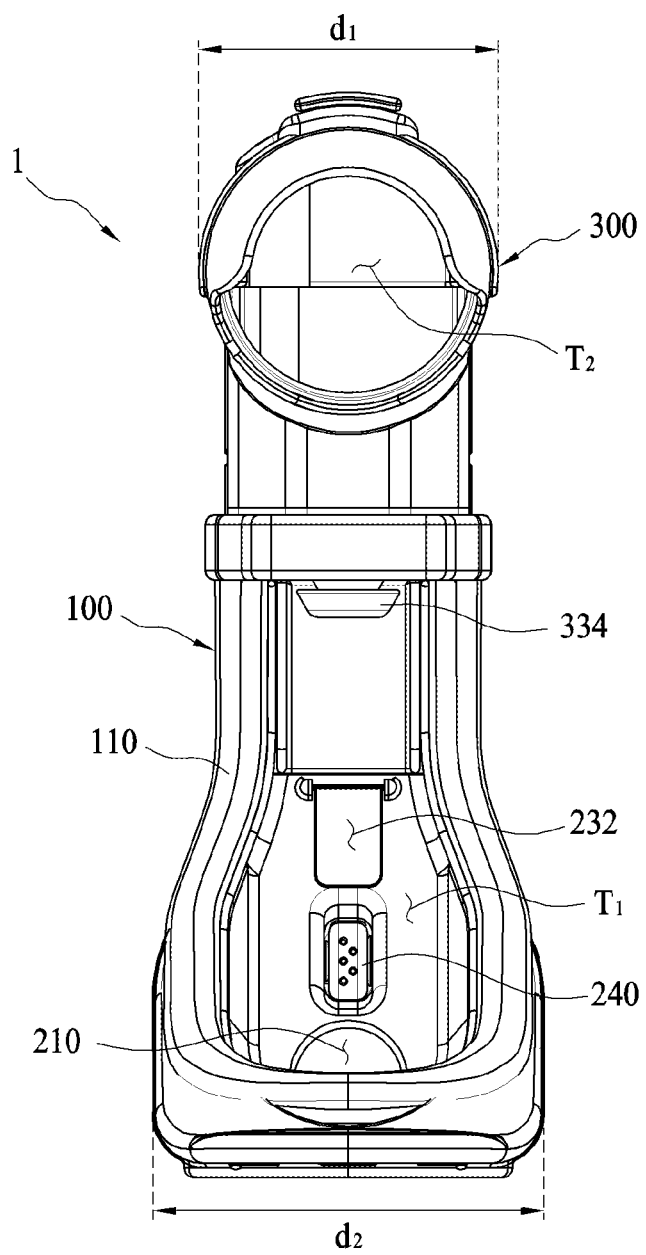
FIG. 4 is a front view of an excreta disposal apparatus according to an embodiment of the present invention.

FIG. 4 is a front view of the excreta disposal apparatus 1 according to an embodiment of the present invention.

FIG. 4 shows the disposal spaces T1 and T2 of the seating portion 100 in more detail. As described above, in the present embodiment, the disposal spaces T1 and T2 include the urine disposal unit T2 and the excrement disposal unit T1. Various elements for disposing of the excreta may be provided in the disposal spaces T1 and T2.

A spray unit is an element that is exposed to the disposal spaces T1 and T2 to spray washing water, and may include one or more spraying nozzles. In the case of the present embodiment, the spray unit is provided with a rotary nozzle 240 for spraying washing water to the excrement disposal unit T1 side, an auxiliary nozzle 334, and, although not shown, an upper side nozzle for spraying washing water to the urine disposal unit T2 side.

That is, the auxiliary nozzle 334 sprays washing water so as to wash the surface of the excrement disposal unit T1. In addition, the upper side nozzle sprays washing water so as to wash the genital area and the surface of the urine disposal unit T2.

In addition, the spray unit includes a washing unit including a rotary nozzle 240, which is provided so as to rotate about a central axis and has, in the circumference thereof, spray holes for spraying the washing water. The washing unit includes a rotary nozzle 240 and elements associated with the rotary nozzle 240, which will be described later.

In addition, in the present embodiment, a drying air jet opening 232 is formed in the disposal space T1 and T2 to allow a drying air to flow and be jetted, thereby rapidly drying the water after washing.

Meanwhile, as shown in the drawing, the body including the seating portion 100 and the main body unit is formed in such a manner that a width d1 of the upper portion is narrower than a width d2 of the lower portion when viewed from the front. That is, it has a shape corresponding to the curved shape of a thigh portion of the human body, so that both legs of the user can be stably adhered to both sides of the body of the excreta disposal apparatus 1. In addition, the body is formed to have a width corresponding to the width between the legs of the user, so that the user can take a natural posture without opening his/her legs forcibly.

In the present embodiment, a fastening member 110 is provided around the seating portion 100 to be in close contact with the user's body. The fastening member 110 is provided in a band shape along the circumferential line of the seating portion 100, so that the feelings of wearing can be improved.

Figure 5:
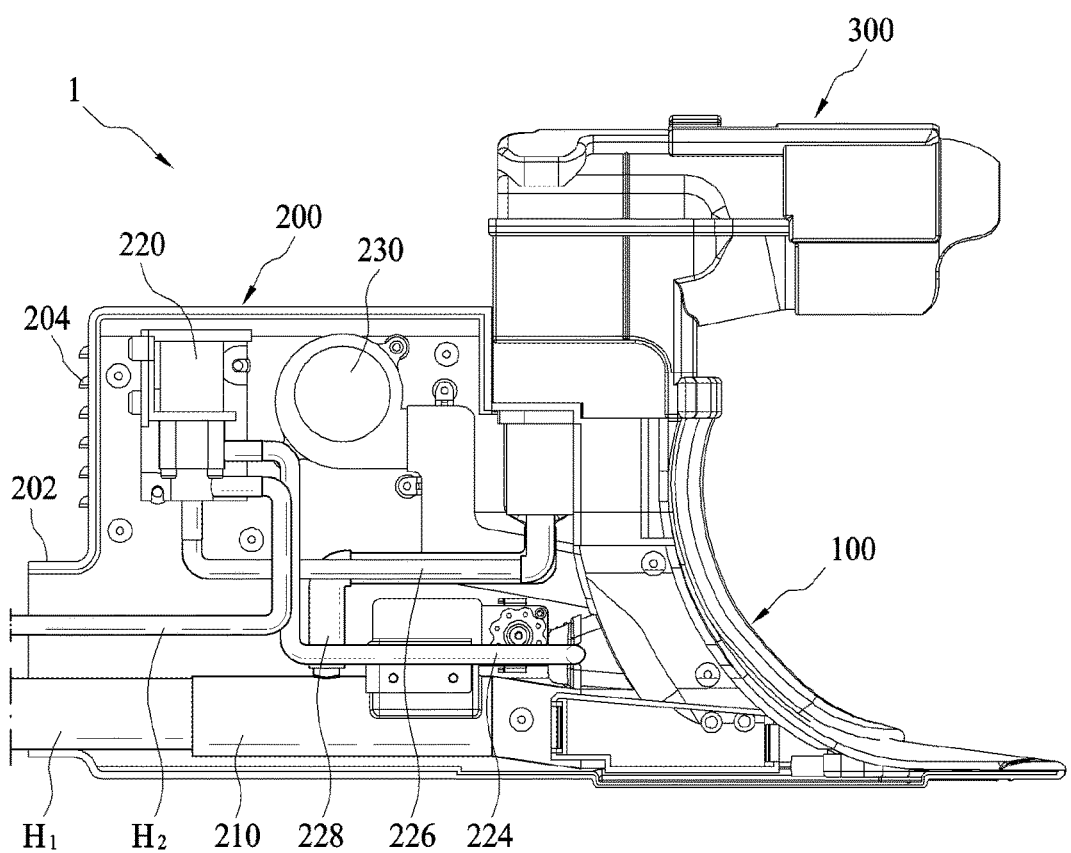
FIG. 5 is a cross-sectional view showing an internal structure of a main body unit in an excreta disposal apparatus according to an embodiment of the present invention.

FIG. 5 is a cross-sectional view showing an internal structure of the main body unit 200 in the excreta disposal apparatus 1 according to an embodiment of the present invention.

As shown in FIG. 5, an accommodation space is formed inside the main body unit 200, and the accommodation space may be provided with various elements. In the present embodiment, the accommodation space is provided with the above mentioned discharge channel 210, a flow channel switching unit 220, and an air blowing unit 230.

The discharge channel 210 is connected to an excreta flow tube H1 that is introduced through the through hole 202 to discharge the excreta to the outside. Particularly, in the present embodiment, the urine received from the male module 300 side can be introduced into the discharge channel 210 through an auxiliary discharge channel 228.

The flow channel switching unit 220 is an element which is connected to a washing water feeding pipe H2 introduced through the through hole 202 and receives the washing water from the outside, and ramifies and supplies the washing water to a plurality of spray nozzles through a solenoid valve or the like. Specifically, in the present embodiment, the washing water stored in the flow channel switching unit 220 may flow to the rotary nozzle through a first supply channel 224 and may flow to the auxiliary nozzle and the upper side nozzle through a second supply channel 226.

The air blowing unit 230 is an element which blows dry air to the disposal space, can generate dry air by using a blowing fan or the like, and can blow the dry air to the disposal space side through the drying air jet opening. Further, a heater may be further provided so as to increase the temperature of the dry air.

In the present embodiment, an air inlet 204 is formed on the rear surface of the main body unit 200 to allow an external air to flow to ventilate the inside of the accommodation space.

The overall configuration of the excreta disposal apparatus according to the present embodiment was described above, and the washing unit of the above-described spray unit will be described in detail below.

Figure 6:
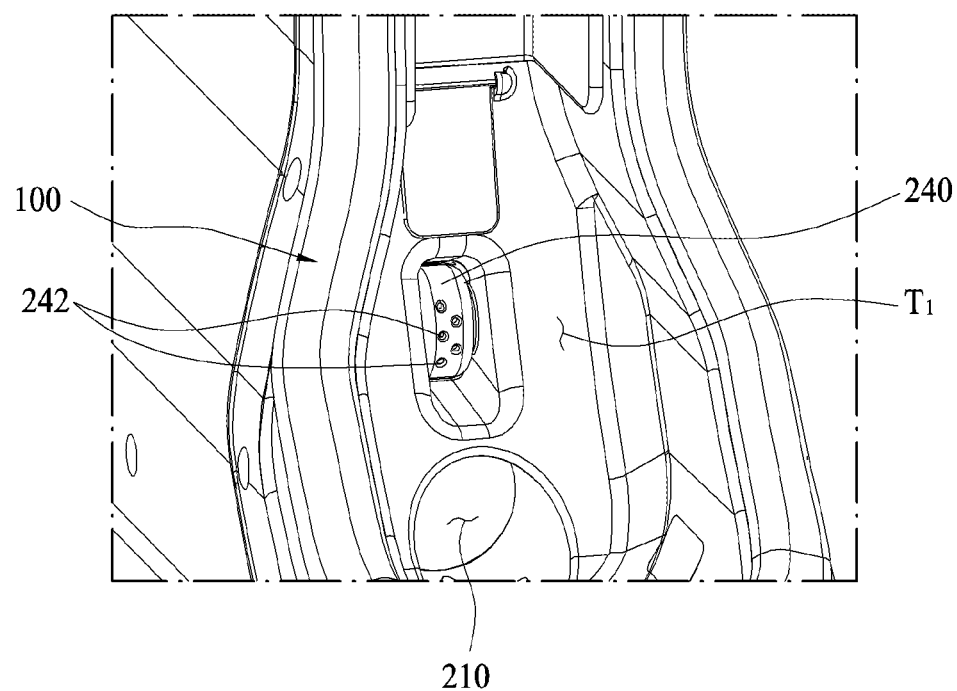
FIG. 6 is a perspective view of a rotary nozzle in an excreta disposal apparatus according to an embodiment of the present invention.

FIG. 6 is a perspective view of the rotary nozzle 240 in the excreta disposal apparatus according to an embodiment of the present invention.

As shown in FIG. 6, the rotary nozzle 240 is exposed to the disposal space, and in particular, in the present embodiment, is exposed to the excrement disposal unit T1. The rotary nozzle 240 is provided so as to rotate about a central axis, and sprays the washing water. One or more spray holes 242 for spraying washing water is formed in the circumference of the rotary nozzle 240.

Particularly, in the present embodiment, the spray holes 242 are arranged in double columns, and the spray holes 242 of each column are alternately arranged so as not to interfere with each other.

The rotation of the rotary nozzle 240 may be performed in various directions. For example, the rotary nozzle 240 may rotate in various directions such as up and down, left and right, and diagonal directions, and may spray the washing water.

Figure 7:
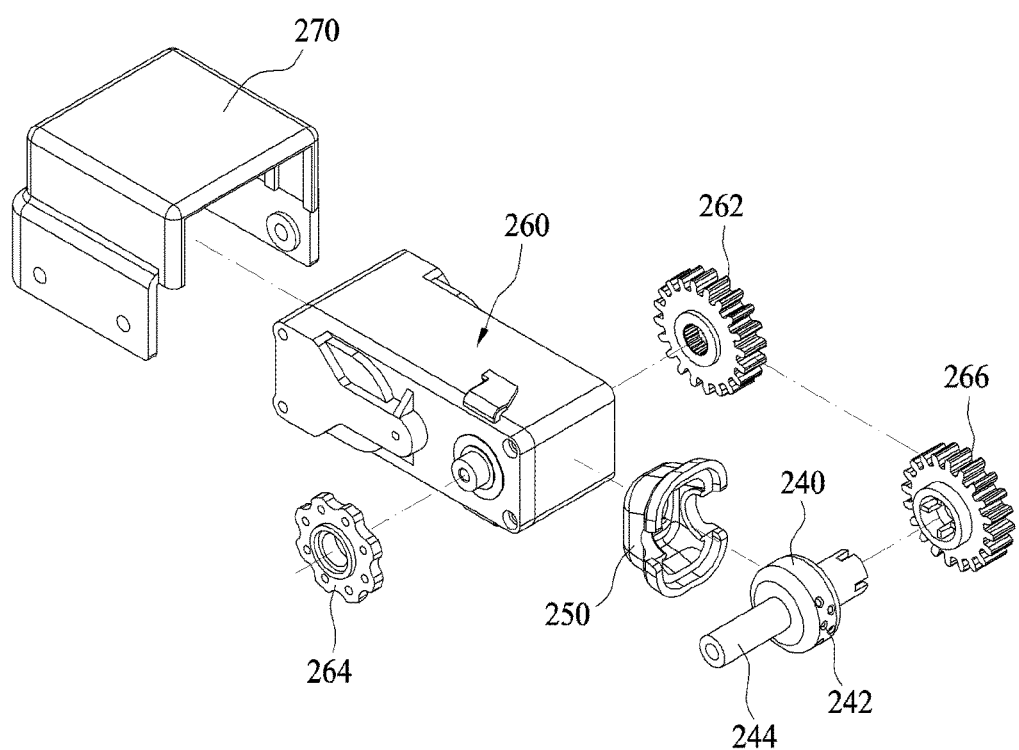
FIG. 7 is a perspective view of a washing unit in an excreta disposal apparatus according to an embodiment of the present invention.

FIG. 7 is a perspective view of the washing unit in the excreta disposal apparatus according to an embodiment of the present invention.

As shown in FIG. 7, the washing unit includes the rotary nozzle 240 and elements associated with the rotary nozzle 240.

In the present embodiment, the washing unit includes the rotary nozzle 240, a motor 260 for generating a rotational driving force, a gear unit 262, 264, 266 which is rotated by the motor 260 and transmits a rotational force to the rotary nozzle 240, a shielding member 250 which receives a part of the rear side of the rotary nozzle 240 and shields the inside of the accommodation space from the disposal space, and a housing 270. Further, although not shown, a controller for controlling each element of the washing unit may be further included.

The gear units 262, 264, 266 may include a plurality of gears, which may be implemented in various forms. The shielding member 250 is formed with a groove for supporting a rotation shaft 244 of the rotary nozzle 240, accommodates a part of the rear side of the rotary nozzle 240, and is mounted in the body of the excreta disposal apparatus, thereby preventing the excreta of the disposal space or the washing water from flowing into the accommodation space. That is, among the elements of the washing unit, the rotary nozzle 240 and the front surface of the shielding member 250 shall be exposed to the disposal space.

The controller is provided to control the movement of the motor 260. When the excreta is detected in the disposal space by a detection sensor or the like, the controller can rotate the motor 260 in the forward and reverse directions, and spray the washing water through the rotary nozzle 240. In addition, it is obvious that the controller may be preset to control the washing unit in various situations.

Meanwhile, a detection sensor including an excrement detection sensor and a urine detection sensor is provided in the disposal space so as to sense the presence or absence of excreta, and to control each element when it is determined that excreta exists.

Figure 8:
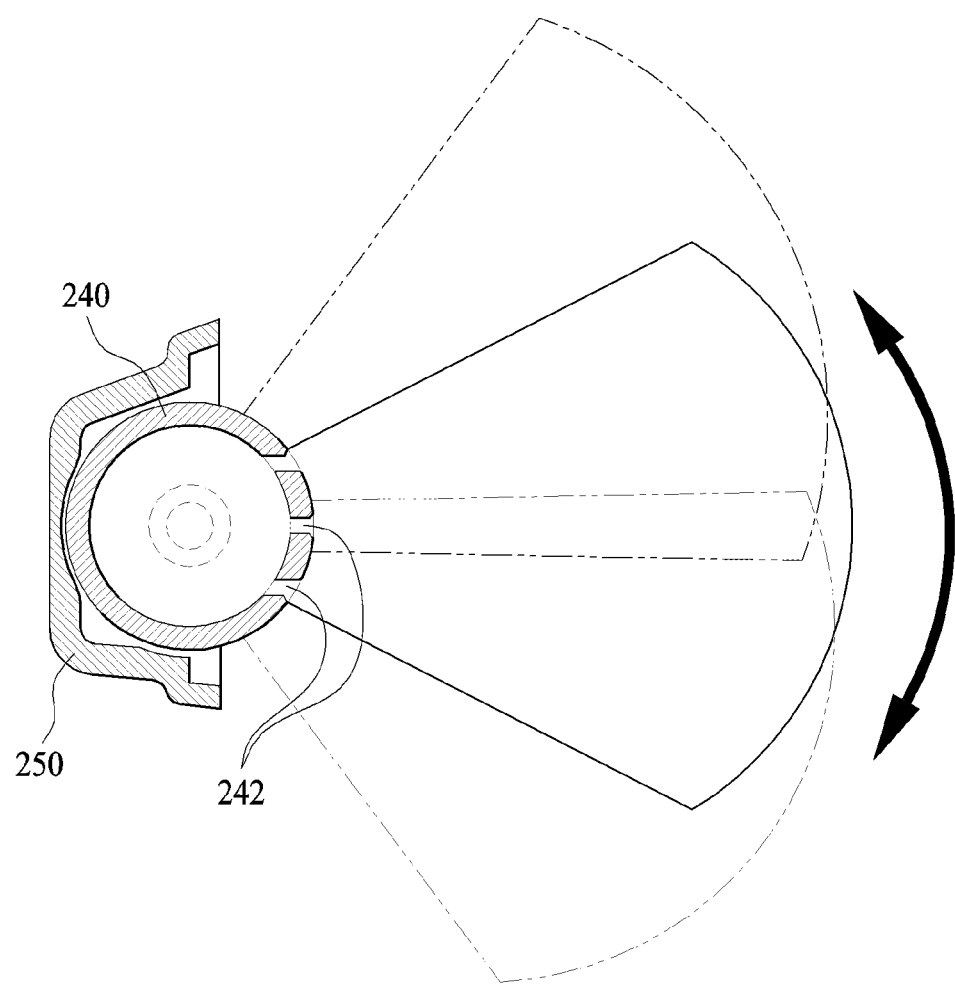
FIG. 8 is a cross-sectional view showing a rotation range in an area where the rotary nozzle is exposed to the disposal space, in an excreta disposal apparatus according to an embodiment of the present invention.

FIG. 8 is a cross-sectional view showing a rotation range in an area where the rotary nozzle 240 is exposed to the disposal space, in the excreta disposal apparatus according to an embodiment of the present invention.

As shown in FIG. 8, the rotary nozzle 240 has a rotation range of a certain angle in an area exposed to the disposal space. In the present embodiment, the rotary nozzle 240 rotates in a range between the upper end and the lower end of the shielding member 250 and is able to spray the washing water to the disposal space and the buttocks or genital area of a user.

That is, according to the present invention, since the rotary nozzle 240 can occupy a very small space and can spray the washing water over a wide range, the overall structure is simplified, the buttocks and genital area of the user can be washed by using only the minimum number of nozzles, and an entire disposal space can be washed.

Meanwhile, for more effective washing, the rotary nozzle 240 may be provided at a position corresponding to a user's anus in a state where the user's body is seated on the seating unit. That is, when the rotary nozzle 240 is provided at a position facing the user's anus, a surrounding area can be uniformly washed around the anus of the user.

More specifically, the rotary nozzle 240 may be provided in such a manner that a center of rotation angle of the area exposed to the excrement disposal unit is provided at a position corresponding to the anus of the user. The reason for this is that the same area in the upper and lower directions around the anus can be washed as the position of facing the anus becomes the center of the rotation angle.

Figure 9:
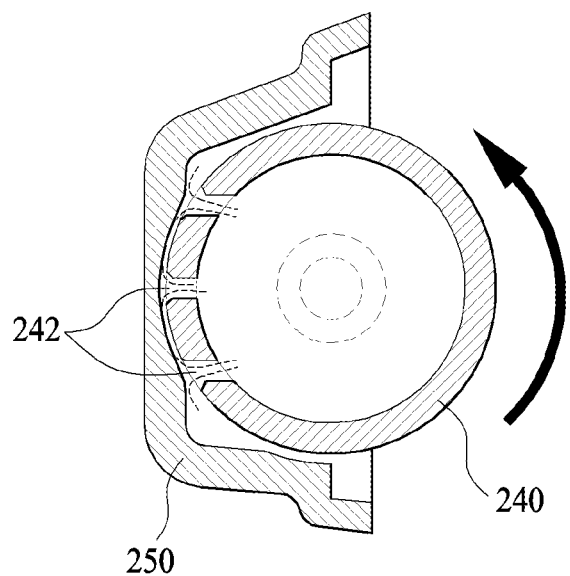
FIG. 9 is a cross-sectional view showing a state in which a rotary nozzle washes a shielding member, in an excreta disposal apparatus according to an embodiment of the present invention.

FIG. 9 is a cross-sectional view showing a state in which a rotary nozzle washes a shielding member, in an excreta disposal apparatus according to an embodiment of the present invention.

As shown in FIG. 9, the rotary nozzle 240 may be rotated so that the spray hole 242 can face the direction of the shielding member 250 to wash the surface of the shielding member 250. That is, since it is difficult to wash manually between the rotary nozzle 240 and the shielding member 250, the shielding member 250 may be washed by the rotary nozzle 240, thereby improving convenience.

This may be implemented by controlling the motor by the controller so as to rotate the rotary nozzle 240 in the direction of the shielding member 250, immediately after the disposal of the excreta is completed.

Although the exemplary embodiments of the present invention have been disclosed for illustrative purposes, those skilled in the art will appreciate that various modifications, additions and substitutions are possible, without departing from the scope and spirit of the invention as disclosed in the accompanying claims. Accordingly, the scope of the present invention is not construed as being limited to the described embodiments but is defined by the appended claims as well as equivalents thereto.

The invention claimed is:

1. An excreta disposal apparatus provided with a rotary nozzle, the apparatus comprising:
  a body comprising a seating unit, which has a shape corresponding to a curved shape of genital area and buttocks of a human body and also has a disposal space open toward the genital area and buttocks of the human body so as to take excreta discharged from the human body, a main body unit, which is connected to the seating unit so as to be mounted between legs of the human body and has an accommodation space therein;
  a discharge channel, which is provided in the accommodation space and communicates with the disposal space so as to discharge the excreta in the disposal space to the outside; and
  a spray unit exposed to the disposal space so as to spray washing water,
  wherein the spray unit is provided at a position facing the user's anus while the user's body is seated on the seating unit, and comprises the rotary nozzle which is rotatable in an up-down direction around a central axis extending in a left-right direction to spray the washing water.

2. The apparatus of claim 1, wherein a spray hole for spraying the washing water is formed in a circumference of the rotary nozzle.

3. The apparatus of claim 1, wherein the disposal space comprises a urine disposal unit corresponding to the genital area of the human body and an excrement disposal unit corresponding to the buttocks of the human body, and the rotary nozzle is exposed to the excrement disposal unit.

4. The apparatus of claim 3, wherein, in the rotary nozzle, a center of rotation angle of the area exposed to the excrement disposal unit is provided at a position corresponding to the user's anus.

5. The apparatus of claim 1, wherein the washing unit comprises:

a motor which generates a rotational driving force; and a gear unit which is rotated by the motor and transmits a rotational force to the rotary nozzle.

6. The apparatus of claim 1, wherein the washing unit comprises a shielding member which receives a part of a rear side of the rotary nozzle and shields the inside of the accommodation space from the disposal space.

7. The apparatus of claim 1, further comprising a controller which controls the washing unit.

8. The apparatus of claim 1, further comprising a flow channel switching unit which is provided in the accommodation space and supplies the washing water introduced from an external to the spray unit.

9. The apparatus of claim 1, further comprising an air blowing unit which is provided in the accommodation space and blows a dry air to the disposal space.

10. The apparatus of claim 1, further comprising a detection sensor which is provided in the disposal space and senses the excreta.

* * * * *